United States Patent [19]

Wick et al.

[11] Patent Number: 5,238,944
[45] Date of Patent: Aug. 24, 1993

[54] TOPICAL FORMULATIONS AND TRANSDERMAL DELIVERY SYSTEMS CONTAINING 1-ISOBUTYL-1H-IMIDAZO[4,5-C]QUINO­LIN-4-AMINE

[75] Inventors: Steven M. Wick, Mahtomedi; Helen J. Schultz, Falcon Heights, both of Minn.; Gregory R. Nelson, Hudson, Wis.; Amit K. Mitra, Woodbury; Stephen M. Berge, Shoreview, both of Minn.

[73] Assignee: Riker Laboratories, Inc., St. Paul, Minn.

[21] Appl. No.: 845,323

[22] Filed: Mar. 3, 1992

Related U.S. Application Data

[63] Continuation of Ser. No. 444,555, Nov. 30, 1989, abandoned, which is a continuation-in-part of Ser. No. 284,933, Dec. 15, 1988, abandoned.

[51] Int. Cl.⁵ .................. A61K 31/44; A61K 31/20
[52] U.S. Cl. ................... 514/293; 514/558; 514/947
[58] Field of Search .......... 514/293, 784, 946, 947, 514/558

[56] References Cited

U.S. PATENT DOCUMENTS

| | | | |
|---|---|---|---|
| 4,411,893 | 10/1983 | Johnson et al. | 514/293 |
| 4,689,338 | 8/1987 | Gerster | 514/293 |
| 4,695,465 | 9/1987 | Kigasawa et al. | 514/947 |
| 4,722,941 | 2/1988 | Eckert et al. | 514/784 |
| 4,746,515 | 5/1988 | Cheng et al. | 424/448 |
| 4,751,087 | 6/1988 | Wick | 514/784 |
| 4,863,970 | 9/1989 | Patel et al. | 514/947 |
| 4,908,389 | 3/1990 | Mahjour et al. | 514/947 |

FOREIGN PATENT DOCUMENTS 8809676 12/1988 PCT Int'l Appl. .

OTHER PUBLICATIONS

J. Pharm. Sci., 1984 (73) 1153 E. R. Cooper.
Yu et al. Pharm. Research (5), 457, 1988.
Loftsson et al. Pharm. Research (4) 346, 1987.
Chien et al. Pharm Research (5) 103, 1988.
Drug Dev. and Ind. Pharmacy, 1987 (13), 2363 Bharguva.
The Theory and Practice of Industrial Pharmacy Lachman, 2nd edition (1976) pp. 220-229.

*Primary Examiner*—Frederick E. Waddell
*Assistant Examiner*—Raymond J. Henley, III
*Attorney, Agent, or Firm*—Gary L. Griswold; Walter N. Kirn; Douglas E. Reedich

[57] ABSTRACT

Pharmaceutical formulations and adhesive-coated sheet materials for the topical and/or transdermal delivery of 1-isobutyl-1H-imidazo[4,5-c]-quinolin-4-amine, including creams, ointments and pressure-sensitive adhesive compositions. Pharmacological methods of using the formulations and the adhesive-coated sheet materials of the invention in the treatment of viral infections.

13 Claims, 1 Drawing Sheet

TOPICAL FORMULATIONS AND TRANSDERMAL DELIVERY SYSTEMS CONTAINING 1-ISOBUTYL-1H-IMIDAZO[4,5-C]QUINOLIN-4-AMINE

This is a continuation of application Ser. No. 07/444,555 filed Nov. 30, 1989, now abandoned, which is a continuation-in-part of U.S. Ser. No. 07/284,933 filed Dec. 15, 1988 now abandoned.

BACKGROUND OF THE INVENTION

1. Field of the Invention

This invention pertains to pharmaceutical formulations for the topical or transdermal delivery of drugs. More particularly, it pertains to creams, ointments, pressure sensitive adhesive coatings, and adhesive-coated sheet materials that contain compounds that enhance skin penetration of drugs.

2. Description of the Related Art

The compound 1-isobutyl-1H-imidazo[4,5-c]-quinolin-4-amine is disclosed in U.S. Pat. No. 4,689,338 and described therein as an antiviral agent and as an interferon inducer. A variety of formulations for topical administration of this compound are also described.

U.S. Pat. No. 4,751,087 discloses the use of a combination of ethyl oleate and glyceryl monolaurate as a skin penetration enhancer for nitroglycerine, with all three components being contained in the adhesive layer of a transdermal patch.

U.S. Pat. No. 4,411,893 discloses the use of N,N-dimethyldodecylamine-N-oxide as a skin penetration enhancer in aqueous systems.

U.S. Pat. No. 4,722,941 discloses readily absorbable pharmaceutical compositions that comprise a pharmacologically active agent distributed in a vehicle comprising an absorption-enhancing amount of at least one fatty acid containing 6 to 12 carbon atoms and optionally a fatty acid monoglyceride. Such compositions are said to be particularly useful for increasing the absorption of pharmacologically active bases.

U.S. Pat. No. 4,746,515 discloses a method of using glyceryl monolaurate to enhance the transdermal flux of a transdermally deliverable drug through intact skin.

SUMMARY OF THE INVENTION

The present invention provides a substantially non-irritating pharmaceutical formulation for topical and/or transdermal administration of the agent 1-isobutyl-1H-imidazo[4,5-c]quinolin-4-amine, which formulation comprises:

a) 1-isobutyl-1H-imidazo[4,5-c]quinolin-4-amine in an amount of about 0.5 percent to about 9 percent by weight based on the total weight of the formulation; and b) a pharmaceutically acceptable vehicle for the 1-isobutyl-1H-imidazo[4,5-c]quinolin-4-amine, which vehicle comprises a fatty acid selected from the group consisting of isostearic acid, oleic acid and a combination thereof in a total amount of about 3 percent to about 45 percent by weight based on the total weight of the formulation. The formulation is further characterized in that when tested in the hairless mouse skin model described herein, the formulation provides a penetration of the agent of at least about 10% (and preferably at least about 15%) of the total amount of the agent contained in the formulation in 24 hours.

The salient elements of a pharmaceutical formulation according to the invention are (a) 1-isobutyl-1H-imidazo[4,5-c]quinolin-4-amine and (b) a fatty acid, i.e., isostearic and/or oleic acid. A pharmaceutical formulation of the invention can be in any form known to the art, such as a cream, an ointment, or a pressure-sensitive adhesive composition, each form containing the necessary elements in particular amounts and further containing various additional elements.

A cream of the invention preferably contains about 1 percent to about 5 percent by weight of 1-isobutyl-1H-imidazo[4,5-c]quinolin-4-amine, based on the total weight of the cream; about 5 percent to about 25 percent by weight of fatty acid, based on the total weight of the cream; and optional ingredients such as emollients, emulsifiers, thickeners, and/or preservatives.

An ointment of the invention contains an ointment base in addition to 1-isobutyl-1H-imidazo[4,5-c]quinolin-4-amine and fatty acid. An ointment of the invention preferably contains about 0.5 percent to about 9 percent, and more preferably about 0.5 percent to about 5 percent by weight 1-isobutyl-1H-imidazo[4,5-c]quinolin-4-amine; about 3 percent to about 45 percent, more preferably about 3 percent to about 25 percent by weight fatty acid; and about 60 percent to about 95 percent by weight ointment base, all weights being based on the total weight of the ointment. Optionally, an ointment of the invention can also contain emulsifiers, emollients and thickeners.

A pressure-sensitive adhesive composition of the invention contains 1-isobutyl-1H-imidazo[4,5-c]-quinolin-4-amine, fatty acid, and an adhesive. The adhesives utilized in a pressure sensitive adhesive composition of the invention are preferably substantially chemically inert to 1-isobutyl-1H-imidazo[4,5-c]quinolin-4-amine. A pressure sensitive adhesive composition of the invention preferably contains about 0.5 percent to about 9 percent by weight, more preferably of about 3 percent to about 7 percent by weight 1-isobutyl-1H-imidazo[4,5-c]quinolin-4-amine; about 10 percent to about 40 percent by weight, more preferably of about 15 percent to about 30 percent by weight, and most preferably about 20 percent to about 30 percent by weight of fatty acid; all weights being based on the total weight of the pressure sensitive adhesive composition.

Optionally, pressure sensitive adhesive compositions of the invention can also contain one or more skin penetration enhancers. The total amount of skin penetration enhancer(s) present in a pressure sensitive adhesive composition of the invention is preferably about 3 percent to about 25 percent by weight, and more preferably about 3 percent to about 10 percent by weight based on the total weight of the pressure sensitive adhesive composition.

A pressure sensitive adhesive coated sheet material of the invention can be made from a pressure-sensitive adhesive composition of the invention in the form of an article such as a tape, a patch, a sheet, or a dressing.

A formulation of the invention can be used to topically and/or transdermally administer 1-isobutyl-1H-imidazo[4,5-c]quinolin-4-amine for treating viral infections, for example Type I or Type II Herpes simplex infections.

BRIEF DESCRIPTION OF THE DRAWING

The invention will be described below with reference to the accompanying Drawing, which is an isometric view of a diffusion cell for measuring penetrability of 1-isobutyl-1H-imidazo[4,5-c]quinolin-4-amine across mammalian skin.

DETAILED DESCRIPTION OF THE INVENTION

As used in the specification and claims, the phrase "substantially non-irritating" designates formulations that do not cause unacceptable skin irritation in conventional repeat skin irritation tests in albino rabbits such as that described in Draize et al., "Appraisal of the Safety of Chemicals in Food, Drugs and Cosmetics", prepared by the Division of Pharmacology of the Food and Drug Administration, published originally in 1959 by the Association of Food and Drug Officials of the United States, Topeka, Kans. (2nd printing 1965), incorporated herein by reference.

The present invention provides pharmaceutical formulations such as creams, ointments and adhesive coatings that contain 1-isobutyl-1H-imidazo[4,5-c]-quinolin-4-amine and a fatty acid such as isostearic and/or oleic acid. The formulations of the invention provide desirable skin penetrability of the 1-isobutyl-1H-imidazo[4,5-c]quinolin-4-amine.

The compound 1-isobutyl-1H-imidazo[4,5-c]-quinolin-4-amine is a known antiviral agent that is also known to induce interferon biosynthesis. It can be prepared using the method disclosed in U.S. Pat. No. 4,689,338, the disclosure of which is incorporated herein by reference. The compound can be used to treat viral infections such as Type I or Type II Herpes simplex infections and genital warts. Furthermore, the fact that the compound is an interferon inducer suggests that it, and therefore formulations containing it, might be useful in the treatment of numerous other diseases, such as rheumatoid arthritis, warts, eczema, hepatitis B, psoriasis, multiple sclerosis, essential thrombocythaemia, and cancer, such as basal cell carcinoma and other neoplastic diseases. The amount of 1-isobutyl-1H-imidazo[4,5-c]quinolin-4-amine present in a formulation of the invention will be an amount effective to treat the targeted disease state to prevent the recurrence of such a disease or to promote immunity against such a disease. The amount is preferably about 0.5 percent to about 9 percent by weight based on the total weight of a formulation.

A fatty acid such as isostearic acid, oleic acid or a mixture thereof is incorporated into a formulation of the invention. The total amount of fatty acid present in a formulation is preferably about 3 percent to about 45 percent by weight based on the total weight of a formulation.

A pharmaceutical formulation of the invention can be in a form such as a cream, an ointment, a pressure-sensitive adhesive composition, or other forms known to those skilled in the art, each particular form containing 1-isobutyl-1H-imidazo[4,5-c]quinolin-4-amine and fatty acid in particular amounts, and optionally containing various additional elements. The preferred amounts of drug and fatty acid, and the amounts and types of optional elements used in formulations of the invention are discussed below with particular reference to creams, ointments, and adhesive compositions.

A cream according to the invention contains 1-isobutyl-1H-imidazo[4,5-c]quinolin-4-amine and fatty acid.

The amount of 1-isobutyl-1H-imidazo[4,5-c]-quinolin-4-amine present in a cream is preferably about 0.5 percent to about 9 percent by weight, and more preferably about 1 percent to about 5 percent by weight, based on the total weight of the cream.

The total amount of fatty acid present in a cream of the invention is preferably about 3 percent to about 45 percent by weight, and more preferably about 5 percent to about 25 percent by weight, based on the total weight of the cream.

Optionally, a cream of the invention can contain emollients, emulsifiers, thickeners, and/or preservatives.

Emollients such as long chain alcohols, e.g., cetyl alcohol, stearyl alcohol and cetearyl alcohol; hydrocarbons such as petrolatum and light mineral oil; or acetylated lanolin can be included in a cream of the invention. A cream can contain one or more of these emollients. The total amount of emollient in a cream of the invention is preferably about 5 percent to about 30 percent, and more preferably about 5 percent to about 10 percent by weight based on the total weight of the cream.

Emulsifiers such as nonionic surface active agents, e.g., polysorbate 60 (available from ICI Americas), sorbitan monostearate, polyglyceryl-4 oleate, and polyoxyethylene(4)lauryl ether or trivalent cationic a cream of the invention. A cream can contain one or more emulsifiers. Generally the total amount of emulsifier is preferably about 2 percent to about 14 percent, and more preferably about 2 percent to about 6 percent by weight based on the total weight of the cream.

Pharmaceutically acceptable thickeners, such as Veegum TM K (available from R. T. Vanderbilt Company, Inc.), and long chain alcohols (i.e. cetyl alcohol, stearyl alcohol or cetearyl alcohol) can be used. A cream can contain one or more thickeners. The total amount of thickener present is preferably about 3 percent to about 12 percent by weight based on the total weight of the cream.

Preservatives such as methylparaben, propylparaben and benzyl alcohol can be present in a cream of the invention. The appropriate amount of such preservative(s) is known to those skilled in the art.

Optionally, an additional solubilizing agent such as benzyl alcohol, lactic acid, acetic acid, stearic acid or hydrochloric acid can be included in a cream of the invention. If an additional solubilizing agent is used, the amount present is preferably about 1 percent to about 12 percent by weight based on the total weight of the cream.

Optionally, a cream of the invention can contain a humectant such as glycerin, skin penetration enhancers such as butyl stearate, and additional solubilizing agents.

It is known to those skilled in the art that a single ingredient can perform more than one function in a cream, i.e., cetyl alcohol can serve both as an emollient and as a thickener.

Generally, a cream consists of an oil phase and a water phase mixed together to form an emulsion. Preferably, the amount of water present in a cream of the invention is about 45 percent to about 85 percent by weight based on the total weight of the cream.

The oil phase of a cream of the invention can be prepared by first combining the 1-isobutyl-1H-imidazo[4,5-c]quinolin-4-amine and the fatty acid (if the cream contains benzyl alcohol it can also be added at this point) and heating with occasional stirring to a temperature of about 50° C. to 85° C. When the 1-isobutyl-1H-imidazo[4,5-c]quinolin-4-amine appears to be completely dissolved, the remaining oil phase ingredients are added and heating is continued until dissolution appears to be complete.

The water phase can be prepared by combining all other ingredients and heating with stirring until dissolution appears to be complete.

The creams of the invention are generally prepared by adding the water phase to the oil phase with both phases at a temperature of about 65° C. to 75° C. The resulting emulsion is mixed with a suitable mixer apparatus to give the desired cream.

An ointment of the invention contains an ointment base in addition to 1-isobutyl-1H-imidazo[4,5-c]quinolin-4-amine and fatty acid.

The amount of 1-isobutyl-1H-imidazo[4,5-c]-quinolin-4-amine present in an ointment of the invention is preferably about 0.5 percent to about 9 percent, and more preferably about 0.5 percent to about 5 percent by weight based on the total weight of the ointment.

The total amount of fatty acid present in an ointment of the invention is preferably about 3 percent to about 45 percent, and more preferably about 3 percent to about 25 percent based on the total weight of the ointment.

A pharmaceutically acceptable ointment base such as petrolatum or polyethylene glycol 400 (available from Union Carbide) in combination with polyethylene glycol 3350 (available from Union Carbide) can be used. The amount of ointment base present in an ointment of the invention is preferably about 60 percent to about 95 percent by weight based on the total weight of ointment.

Optionally, an ointment of the invention can also contain emollients, emulsifiers and thickeners. The emollients, emulsifiers, and thickeners and the preferred amounts thereof described above in connection with creams are also generally suitable for use in an ointment of the invention.

An ointment according to the invention can be prepared by combining 1-isobutyl-1H-imidazo[4,5-c]quinolin-4-amine with fatty acid and heating with occasional stirring to a temperature of about 65° C. When the 1-isobutyl-1H-imidazo[4,5-c]-quinolin-4-amine appears to be completely dissolved, the remaining ingredients are added and heated to about 65° C. The resulting mixture is mixed with a suitable mixer while being allowed to cool to room temperature.

A pressure-sensitive adhesive composition of the invention contains 1-isobutyl-1H-imidazo[4,5-c]quinolin-4-amine, fatty acid, and a pressure sensitive adhesive polymer.

The amount of 1-isobutyl-1H-imidazo[4,5-c]quinolin-4-amine present in a pressure sensitive adhesive composition of the invention is preferably about 0.5 percent to about 9 percent by weight, and more preferably about 3 percent to about 7 percent by weight based on the total weight of the adhesive composition. The amount of fatty acid present is preferably about 10 percent to about 40 percent by weight, more preferably about 15 percent to about 30 percent by weight, and most preferably about 20 percent to about 30 percent by weight, based on the total weight of the adhesive composition.

Preferably, the adhesive polymer utilized in a pressure sensitive adhesive composition of the invention is substantially chemically inert to 1-isobutyl-1H-imidazo[4,5-c]quinolin-4-amine. The adhesive polymer is preferably present in an amount of about 55 percent to about 85 percent by weight based on the total weight of the composition. Suitable adhesive polymers include acrylic adhesives that contain, as a major constituent (i.e., at least about 80 percent by weight of all monomers in the polymer), a hydrophobic monomeric acrylic or methacrylic acid ester of an alkyl alcohol, the alkyl alcohol containing 4 to 10 carbon atoms. Examples of suitable monomers are those discussed below in connection with the "A Monomer". These adhesive polymers can further contain minor amounts of other monomers such as the "B Monomers" listed below.

Preferred adhesives include acrylic pressure-sensitive adhesive copolymers containing A and B Monomers as follows: Monomer A is a hydrophobic monomeric acrylic or methacrylic acid ester of an alkyl alcohol, the alkyl alcohol containing 4 to 10 carbon atoms, preferably 6 to 10 carbon atoms, more preferably 6 to 8 carbon atoms, and most preferably 8 carbon atoms. Examples of suitable A Monomers are n-butyl, n-pentyl, n-hexyl, isoheptyl, n-nonyl, n-decyl, isohexyl, 2-ethyloctyl, isooctyl and 2-ethylhexyl acrylates. The most preferred A Monomer is isooctyl acrylate.

Monomer B is a reinforcing monomer selected from the group consisting of acrylic acid; methacrylic acid; alkyl acrylates and methacrylates containing 1 to to 3 carbon atoms in the alkyl group; acrylamide; methacrylamide; lower alkyl-substituted acrylamides (i.e., the alkyl group containing 1 to 4 carbon atoms) such as tertiary-butyl acrylamide; diacetone acrylamide; n-vinyl-2-pyrrolidone; vinyl ethers such as vinyl tertiary-butyl ether; substituted ethylenes such as derivatives of maleic anhydride, dimethyl itaconate and monoethyl formate and vinyl perfluoro-n-butyrate. The preferred B Monomers are acrylic acid, methacrylic acid, the above-described alkyl acrylates and methacrylates, acrylamide, methacrylamide, and the above-described lower alkyl substituted acrylamides. The most preferred B Monomer is acrylamide.

In one embodiment of a pressure-sensitive adhesive composition of the invention, the pressure-sensitive adhesive copolymer containing A and B Monomers as set forth above preferably contains the A Monomer in an amount by weight of about 80 percent to about 98 percent of the total weight of all monomers in the copolymer. The A Monomer is more preferably present in an amount by weight of about 88 percent to about 98 percent, and is most preferably present in an amount by weight of about 91 percent to about 98 percent. The B Monomer in such a copolymer is preferably present in the pressure-sensitive adhesive copolymer in an amount by weight of about 2 percent to about 20 percent, more preferably about 2 percent to about 12 percent, and most preferably 2 to 9 percent of the total weight of the monomers in the copolymer.

In another embodiment of a pressure-sensitive adhesive composition of the invention, the adhesive copolymer comprises about 60 to about 80 percent by weight (and preferably about 70 to about 80 percent by weight) of the above-mentioned hydrophobic monomeric acrylic or methacrylic acid ester of an alkyl alcohol (i.e., Monomer A described above) based on the total weight of all monomers in the copolymer; about 4 to about 9 percent by weight based on the total weight of all monomers in the copolymer of a reinforcing monomer selected from the group consisting of acrylic acid, methacrylic acid, an alkyl acrylate or methacrylate containing 1 to 3 carbon atoms in the alkyl group, acrylamide, methacrylamide, a lower alkyl-substituted acrylamide, diacetone acrylamide and N-vinyl-2-pyrrolidone; and about 15 to about 35 percent by weight (and preferably about 15 to about 25 percent by weight) of vinyl acetate based on the total weight of all monomers in the copolymer. In this embodiment the preferred acrylic or methacrylic acid ester is isooctyl acrylate and the preferred reinforcing monomer is acrylamide.

The above described adhesive copolymers are known, and methods of preparation therefor are well known to those skilled in the art, having been described for example, in U.S. Pat. No. 24,906 (Ulrich), the disclosure of which is incorporated herein by reference. The polymerization reaction can be carried out using a free radical initiator such as an organic peroxide (e.g., benzoylperoxide) or an organic azo compound (e.g., 2,2'-azobis(2,4-dimethylpentanenitrile), available under the trade designation "Vazo 52" from DuPont).

Since pressure-sensitive adhesives such as those described above are inherently rubbery and tacky and are suitably heat and light stable, there is no need to add tackifiers or stabilizers. However, such can be added if desired.

Optionally, a pressure sensitive adhesive composition of the invention can also contain one or more skin penetration enhancers such as glyceryl monolaurate, ethyl oleate, isopropyl myristate, diisopropyl adipate and N,N-dimethyldodecylamine-N-oxide, either as a single ingredient or as a combination of two or more ingredients. The skin penetration enhancer(s) preferably form a substantially homogeneous mixture with the pressure sensitive adhesive polymer or copolymer. The total amount of skin penetration enhancer(s) present in a pressure sensitive adhesive composition of the invention is preferably about 3 percent to about 25 percent by weight, more preferably about 3 percent to about 10 percent by weight based on the total weight of the adhesive composition.

When the skin penetration enhancer is a single ingredient, it is preferably a skin penetration enhancer such as isopropyl myristate, diisopropyl adipate, ethyl oleate, or glyceryl monolaurate.

When a combination skin penetration enhancer is used, it is preferably a combination such as: ethyl oleate with glyceryl monolaurate; ethyl oleate with N,N-dimethyldodecylamine-N-oxide; glyceryl monolaurate with N,N-dimethyldodecylamine-N-oxide; and ethyl oleate with both glyceryl monolaurate and N,N-dimethyldodecylamine-N-oxide.

A pressure-sensitive adhesive composition of the invention can be prepared by combining dry adhesive, 1-isobutyl-1H-imidazo[4,5-c]quinolin-4-amine, fatty acid, and skin penetration enhancer(s) with an organic solvent. The preferred organic solvents are methanol and ethyl acetate. The total solids content of the adhesive coating is preferably in the range of about 15 percent to about 40 percent, and more preferably in the range of about 20 to about 35 percent based on the total weight of the adhesive coating. The resulting mixture is shaken or mixed for a period of about 20 to 72 hours. When this method is used it is preferred that the 1-isobutyl-1H-imidazo[4,5-c]-quinolin-4-amine be in micronized form (i.e., particle size of 1-2 microns in diameter). Optionally, the mixture can be heated during shaking.

In a preferred method, the 1-isobutyl-1H-imidazo-4,5-c]quinolin-4-amine is combined with the fatty acid and shaken at 40° C. until there appears to be complete dissolution. The remaining ingredients are added and the mixture is shaken for a period of about 20 to 72 hours.

The pressure-sensitive adhesive compositions described above are preferably coated onto one surface of a suitable backing of sheet material, such as a film, to form a pressure-sensitive adhesive coated sheet material. A pressure-sensitive adhesive coated sheet material of the invention can be prepared by knife coating a suitable release liner to a predetermined uniform thickness with a wet adhesive formulation. This adhesive coated release liner is then dried and laminated onto a backing using conventional methods. Suitable release liners include conventional release liners comprising a known sheet material, such as a polyester web, a polyethylene web, or a polystyrene web, or polyethylene-coated paper, coated with a suitable silicone-type coating such as that available under the trade designation Daubert 164Z, from Daubert Co. The backing can be occlusive, non-occlusive or a breathable film as desired. The backing can be any of the conventional materials for pressure-sensitive adhesive tapes, such as polyethylene, particularly low density polyethylene, linear low density polyethylene, high density polyethylene, randomly-oriented nylon fibers, polypropylene, ethylene-vinylacetate copolymer, polyurethane, rayon and the like. Backings that are layered, such as polyethylene-aluminum-polyethylene composites are also suitable. The backing should be substantially non-reactive with the ingredients of the adhesive coating. The presently preferred backing is low density polyethylene.

The pressure-sensitive adhesive coated sheet material of the invention can be made in the form of an article such as a tape, a patch, a sheet, a dressing or any other form known to those skilled in the art.

Preferably, an article in the form of a patch is made from an adhesive coated sheet material of the invention and applied to the skin of a mammal. The patch is replaced as necessary with a fresh patch to maintain the particular desired therapeutic effect of the 1-isobutyl-1H-imidazo[4,5-c]quinolin-4-amine.

The following test methods have been employed in the examples which thereafter follow.

In Vitro Test Method

Figure 1:
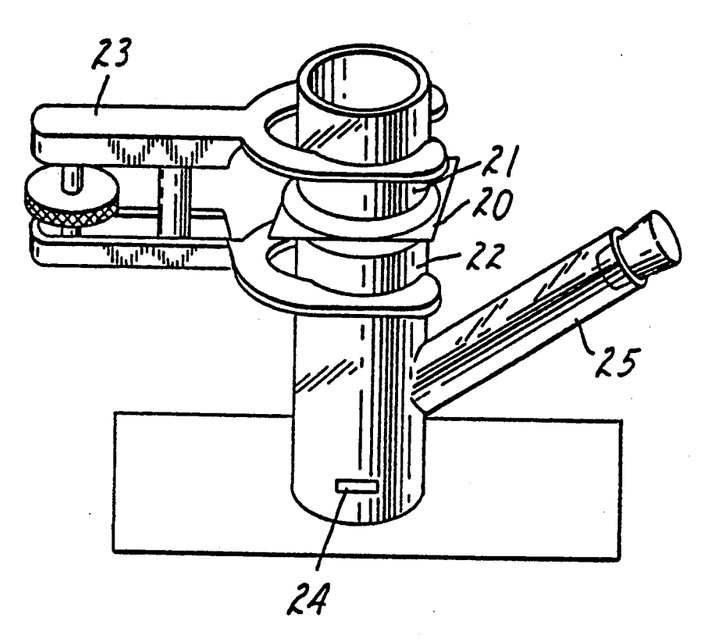

Although animal skins are known to give significant quantitative differences in drug penetrability as compared to human skin, a rank order correlation is generally observed with various drugs (M. J. Bartek and J. A. LaBudde in "Animal Modes in Dermatology", H. Maibach, Ed., Churchill Livingstone, New York, 1975, pp. 103-119). Hairless mouse skin has been recommended as a readily available animal skin for use in diffusion cells with steroids and other small molecules (R. B. Stoughton, Arch. Derm., 99, 753 (1969), J. L. Cohen and R. B. Stoughton, J. Invest. Derm. 62, 507 (1974), R. B. Stoughton in "Animal Modes in Dermatology", pp. 121-131). In the specific test procedure used herein, hairless mouse skin removed from female hairless mice that were 40-80 days old (available from Jackson Laboratory, Strain HRS/J) was used. The skin was maintained on ice until use, and it was preferably used within 8 hours of sacrifice. The mouse skin was mounted on a diffusion cell of the type shown in the Drawing. The cell is modeled after those described in the literature, e.g., J. L. Cohen, R. B. Stoughton, J. Invest. Derm., 62, 507 (1974) and R. B. Stoughton, Arch. Derm., 99, 753 (1964). As shown in the Drawing, the mouse skin 20 was mounted epidermal side up between upper and lower portions of the cell 21 and 22, which are held together by means of a ball joint clamp 23.

The portion of the cell below the mounted skin was completely filled with 0.1 N hydrochloric acid such that the receptor fluid contacted the skin. The receptor fluid was stirred using a magnetic stir bar 24 and a magnetic stirrer (not illustrated). The sampling port 25 was covered with a material such as Parafilm® except when in use.

When a cream or ointment was evaluated, approximately 100 mg of the formulation was applied to the epidermal (upper) side of the skin to cover in an even layer only the area of the skin that would be in contact with the receptor fluid when the skin is mounted in the diffusion cell. When an adhesive coated sheet material was evaluated, the skin was mounted on the diffusion cell and a 2.056 cm$^2$ patch was applied to the skin and pressed to cause uniform contact to the skin. Generally, the cream or the patch was applied to the skin prior to the time the receptor fluid was added to the cell below the skin.

The cell was then placed in a constant temperature ($32°\pm2°$ C.) chamber. To maintain constant temperature, the chamber utilized a heat exchanger coupled to a constant temperature bath, with a fan to circulate air. The receptor fluid was stirred by means of a magnetic stirring bar throughout the experiment to assure a uniform sample and a reduced diffusion barrier layer on the dermal side of the skin. A sample of receptor fluid was removed at specified times. The withdrawn receptor fluid was analyzed for drug content by conventional high pressure liquid chromatography as follows:

A 15 centimeter column containing Zorbax TM C$_8$ (an octylsilane, available from E. I. DuPont de Nemours & Company), 5 micron particle size, was used. The mobile phase was 35 percent acetonitrile/65 percent water (volume/volume) containing 0.2 percent tetramethylammonium hydroxide and 0.2 percent 1-dodecanesulfonate sodium, with the pH of the mobile phase adjusted to 2.0 with phosphoric acid. The flow rate was 2 ml per minute. Ultraviolet detection at 254 nanometers was used. The amount of drug penetrating the skin over the specified time period was calculated as a percentage of the dose applied to the skin.

This in vitro method is referred to as the hairless mouse skin model in the claims. For purposes of the claims where this model is referred to the values stated for skin penetration are the average of 4 independent determinations using a different mouse skin for each determination.

In Vivo Test Method

Formulations of the invention can also be evaluated in vivo for their ability to inhibit lesion formation in guinea pigs infected with Herpes simplex virus Type II and for their ability to induce interferon production in guinea pigs.

In the specific test method used herein, care was taken to be sure the formulation had optimal penetration by washing the backs of the guinea pigs with mild detergent before the formulations were applied. One treatment was given at 24 hours preinfection. When a cream or ointment was evaluated, 200 microliters of the formulation was applied topically to the back of the guinea pig, rubbed in, covered with a Hill-top Chamber and then wrapped with Medipore TM brand tape (commercially available from 3M). When an adhesive coated sheet material was evaluated, an article in the form of a patch of a specified size was applied to the back of the guinea pig and wrapped with Medipore TM brand tape. After the patch had been in place for 24 hours, it was removed and the guinea pig was infected with the virus as described below.

Female Hartley guinea pigs (150–200 grams) were abraded in the vaginal area with a dry cotton swab. The guinea pigs were then infected intravaginally with a cotton swab saturated with HSV-2 ($1\times10^{-5}$ plaque forming units/ml). The formulations of the invention were evaluated by comparing lesion development in treated and untreated animals. External lesions were scored daily for ten days, unless otherwise specified, using the following scale: 0, no lesion; 1, redness and swelling; 2, a few small vesicles; 3, several large vesicles; 4, large ulcers and necrosis; 5, paralysis. The percent Lesion Inhibition was calculated as follows $100-[(\text{Sum of maximum lesion scores of treated group divided by the Sum of the maximum scores of infected control})\times100]$.

Interferon levels in the guinea pigs was monitored by bleeding via cardiac puncture of anesthetized guinea pigs 17 to 24 hours after dosing. The serum of each animal was separately assayed for interferon activity as follows:

The serum was diluted and incubated with guinea pig fibroblast cells at 37° C. overnight in 96 well microtiter plates. The incubated cells were then challenged with an inoculum of mengovirus that is sufficient to kill untreated cells in two days. Two days after such a challenge, the cells were examined both microscopically and after staining with crystal violet to determine whether the cells remain intact The results were reported as activity/ml. Activity/ml indicates the highest dilution of serum that protects cells from virus challenge. An untreated guinea pig control typically exhibits an activity/ml of less than about 100, although activity/ml has been observed to exceed 100.

Inherent Viscosity Measurement

The inherent viscosity values reported in the Examples below were obtained by the conventional method used by those skilled in the art. The measurement of the viscosity of dilute solutions of the adhesive, when compared to controls run under the same conditions, clearly demonstrates the relative molecular weights. It is the comparative values that are significant; absolute figures are not required. In the examples, the inherent viscosity values were obtained using a Cannon-Fenske #50 viscometer to measure the flow time of 10 ml of a polymer solution (0.2 g polymer/deciliter tetrahydrofuran, in a water bath controlled at 25° C.). The examples and the controls were run under identical conditions. The test procedure followed and the apparatus used are explained in detail in the *Textbook of Polymer Science*, F. W. Billmeyer, Wiley-Interscience, 2nd Edition, 1971 under: Polymer chains and their characterization, D. Solution Viscosity and Molecular Size, pp 84–85, the disclosure of which is incorporated by reference.

The following examples are provided to illustrate the invention, but are not intended to be limiting thereof. Parts and percentages are by weight unless otherwise specified.

PREPARATIVE METHOD 1

Laboratory Scale Preparation of Isooctylacrylate/Acrylamide Copolymer

To a 114 gram narrow-mouth glass bottle were added: 18.6 g isooctyl acrylate, 1.4 g acrylamide, 0.04 g benzoyl peroxide, 27.0 g ethyl acetate and 3.0 g methanol. The solution was purged for thirty five seconds with nitrogen at a flow rate of one liter per minute. The bottle was sealed and placed in a rotating water bath at 55° C. for twenty-four hours to effect essentially complete polymerization. The polymer was diluted with ethyl acetate/methanol (90/10) to 23.2 percent solids and had a measured inherent viscosity of 1.26 dl/g in ethyl acetate.

PREPARATIVE METHOD 2

Pilot Plant Scale Preparation of Isooctylacrylate/Acrylamide Copolymer 155 kg isooctylacrylate, 11.6 kg acrylamide, 209.1 kg ethyl acetate and 23.2 kg methanol were charged to a clean, dry reactor. Medium agitation was applied. The batch was deoxygenated with nitrogen while heating to an induction temperature of 55° C. 114 g Lucidol TM 70 initiator (available from Pennwalt Corp.) mixed with 2.3 kg ethyl acetate was charged to the reactor. The temperature was maintained at 55° C. throughout the reaction. After 5.5 hours reaction time, 114 g Lucidol TM 70 mixed with 2.3 kg ethyl acetate were charged to the reactor. After 9.0 hours reaction time, an additional 114 g Lucidol TM 70 initiator mixed with 2.3 kg ethyl acetate were charged to the reactor. The reaction was continued until the percent conversion was greater than 98 percent as measured by gas chromatographic evaluation of residual monomer concentration. The resulting polymer solution was diluted to 25–28 percent solids with ethyl acetate/methanol (90/10) and had a measured Brookfield viscosity of 17,000–21,000 centipoises using spindle #4 at 12 rpm. The polymer had a measured inherent viscosity of 1.3–1.4 dl/g in ethyl acetate.

The above procedure was found to provide a pressure-sensitive adhesive that is equivalent in the practice of the present invention to a pressure-sensitive adhesive prepared according to PREPARATIVE METHOD 1.

A 25–30 percent solids solution of the isooctyl acrylate:acrylamide (93:7) adhesive copolymer in ethyl acetate/methanol (90:10) was coated onto a two-sided release liner using a knife-coater and coating at 0.5 mm in thickness. The adhesive-coated laminate was dried first at 82° C. for 3 minutes and then at 116° C. for 3 minutes. The dried adhesive coating was then stripped off the release liner and placed in a glass bottle. The foregoing procedure results in a reduction of the amount of any residual monomer in the adhesive copolymer.

PREPARATIVE METHOD 3

Preparation of Isooctyl Acrylate: Acrylamide: Vinyl Acetate (75:5:20) Copolymer The procedure of PREPARATIVE METHOD 1 above acrylate, 8.0 g acrylamide, 32.0 g vinyl acetate, 0.32 g benzoyl peroxide, 216.0 g ethyl acetate and 24.0 g methyl alcohol. The resulting polymer was diluted with the ethyl acetate/methyl alcohol mixture to 21.52% solids. The adhesive polymer had a measured inherent viscosity of 1.40 dl/g in ethyl acetate at a concentration of 0.15 g/dl. Its Brookfield viscosity was 2,300 centipoise.

PREPARATIVE METHOD 4

Preparation of Isooctyl Acrylate Acrylamide: Vinyl Acetate (75:5:20) Copolymer A master batch was prepared by combining 621.0 g of isooctyl acrylate, 41.4 g of acrylamide, 165.6 g of vinyl acetate, 1.656 g of 2,2'-azobis(2,4-dimethylpentanenitrile) (available from the DuPont Company as Vazo TM 52), 884.52 g of ethyl acetate and 87.48 g of methanol. A 400 g portion of the resulting solution was placed in an amber quart bottle. The bottle was purged for two minutes with nitrogen at a flow rate of one liter per minute. The bottle was sealed and placed in a rotating water bath at 45° C. for twenty-four hours to effect essentially complete polymerization. The copolymer was diluted with 250 g of ethyl acetate/methanol (90/10) to 26.05% solids and had a measured inherent viscosity of 1.27 dl/g in ethyl acetate at a concentration of 0.15 g/dl. Its Brookfield viscosity was 5580 centipoise.

EXAMPLE 1

A cream according to the present invention was prepared from the following ingredients:

| | % by Weight | Amount |
|---|---|---|
| Oil Phase | | |
| 1-Isobutyl-1H-imidazo[4,5-c]-quinolin-4-amine | 1.0 | 40.0 g |
| Isostearic acid | 10.0 | 400.0 g |
| Benzyl alcohol | 2.0 | 80.0 g |
| Cetyl alcohol | 2.2 | 88.0 g |
| Stearyl alcohol | 3.1 | 124.0 g |
| Polysorbate 60 | 2.55 | 102.0 g |
| Sorbitan monostearate | 0.45 | 18.0 g |
| Aqueous Phase | | |
| Glycerin | 2.0 | 80.0 g |
| Methylparaben | 0.2 | 8.0 g |
| Propylparaben | 0.02 | 0.8 g |
| Purified water | 76.48 | 3059.2 g |

The materials listed above were combined according to the following procedure:

The glycerin, methylparaben, propylparaben and water were weighed into a 4 liter glass beaker then heated on a hot plate with stirring until the parabens isostearic acid and 1-isobutyl-1H-imidazo[4,5-c]-quinolin-4-amine were weighed into an 8 liter stainless steel beaker and heated on a hot plate until the amine was in solution (the temperature reached 69° C.). The benzyl alcohol, cetyl alcohol, stearyl alcohol, polysorbate 60 and sorbitan monostearate were added to the isostearic acid solution and heated on a hot plate until all material was dissolved (the temperature reached 75° C.). With both phases at approximately the same temperature (65°–75° C.), the water phase was added to the oil phase. The mixture was mixed with a homogenizer for 13 minutes then put into a cool water bath and mixed with a 3 inch propeller for 40 minutes (the temperature was 29° C.). The resulting cream was placed in glass jars.

EXAMPLES 2–9

Using the general method of Example 1, the cream formulations shown in Tables 1 and 2 were prepared.

TABLE 1

| | % by Weight Example | | | |
|---|---|---|---|---|
| | 2 | 3 | 4 | 5 |
| Oil Phase | | | | |
| 1-Isobutyl-1H-imidazo-[4,5-c]quinolin-4-amine | 1.0 | 1.0 | 1.0 | 1.0 |
| Isostearic acid | 10.0 | 10.0 | 5.0 | 5.0 |
| Benzyl alcohol | — | 2.0 | — | — |
| Cetyl alcohol | — | 1.7 | — | — |
| Stearyl alcohol | — | 2.3 | — | — |
| Cetearyl alcohol | 6.0 | — | 6.0 | 6.0 |
| Polysorbate 60 | 2.55 | 2.55 | 2.55 | 2.55 |
| Sorbitan monostearate | 0.45 | 0.45 | 0.45 | 0.45 |
| Brij TM 30ª | — | — | — | 10.0 |
| Aqueous Phase | | | | |
| Glycerin | 2.0 | 2.0 | 2.0 | 2.0 |
| Methylparaben | 0.2 | 0.2 | 0.2 | 0.2 |
| Propylparaben | 0.02 | 0.02 | 0.02 | 0.02 |
| Purified water | 77.78 | 77.78 | 82.78 | 72.78 |

Brij TM 30 (polyoxyethylene(4) lauryl ether) is available from ICI Americas, Inc.

TABLE 2

| | % by Weight Example | | | |
|---|---|---|---|---|
| | 6 | 7 | 8 | 9 |
| Oil Phase | | | | |
| 1-Isobutyl-1H-imidazo-[4,5-c]quinolin-4-amine | 1.0 | 1.0 | 1.0 | 1.0 |
| Isostearic acid | 10.0 | 25.0 | 10.0 | 6.0 |
| Benzyl alcohol | — | 2.0 | — | 2.0 |
| Cetyl alcohol | — | 2.2 | 1.7 | — |
| Stearyl alcohol | — | 3.1 | 2.3 | — |
| Cetearyl alcohol | 6.0 | — | — | 6.0 |
| Polysorbate 60 | 2.55 | 3.4 | 2.55 | 2.55 |
| Sorbitan monostearate | 0.45 | 0.6 | 0.45 | 0.45 |
| Brij TM 30 | 10.0 | — | — | — |
| Aqueous Phase | | | | |
| Glycerin | 2.0 | 2.0 | 2.0 | 2.0 |
| Methylparaben | 0.2 | 0.2 | 0.2 | 0.2 |
| Propylparaben | 0.02 | 0.02 | 0.02 | 0.02 |
| Purified water | 67.78 | 60.48 | 79.78 | 79.78 |

EXAMPLE 10

A cream according to the present invention was prepared from the following ingredients:

| | % by Weight | Amount |
|---|---|---|
| Oil Phase | | |
| 1-Isobutyl-1H-imidazo[4,5-c]-quinolin-4-amine | 1.0 | 3.00 g |
| Isostearic acid | 5.0 | 15.0 g |
| White petrolatum | 15.0 | 45.0 g |
| Light mineral oil | 12.8 | 38.4 g |
| Aluminum stearate | 8.0 | 24.0 g |
| Cetyl alcohol | 4.0 | 12.0 g |
| Witconol TM 14ª | 3.0 | 9.00 g |
| Acetylated lanolin | 1.0 | 3.0 g |
| Propylparaben | 0.063 | 0.19 g |
| Aqueous Phase | | |
| Veegum TM K[b] | 1.0 | 3.0 g |
| Methylparaben | 0.12 | 0.36 g |
| Purified water | 49.017 | 147.05 g |

ªWitconol TM 14 (polyglyceryl-4 oleate) is available from Witco Chemical Corp. Organics Division
[b]Veegum TM K (colloidal magnesium aluminum silicate) is available from R. T. Vanderbilt Company Inc.

The materials listed above were combined according to the following procedure:

The 1-isobutyl-1H-imidazo[4,5-c]quinolin-4-amine and theisostearic acid were weighed into a glass jar and heated with occasional stirring until the amine was dissolved (the temperature reached 68° C.). To this solution was added, the petrolatum, mineral oil, aluminum stearate, cetyl alcohol, Witconol TM 14, acetylated lanoline and propylparaben. The mixture was heated to 75° C. In a separate beaker, the methylparaben and water were combined and heated until the paraben dissolved (the temperature reached 61° C.). The Veegum TM K was added to the aqueous solution and heated at 75° C. for 30 minutes while mixing with a homogenizer. With both phases at 75° C., the aqueous phase was slowly added to the oil phase while mixing with a homogenizer. Mixing was continued for 30 minutes while maintaining a temperature to about 80° C. The jar was then capped and the formulation was allowed to cool.

EXAMPLE 11

An ointment according to the present invention was prepared from the following ingredients:

| | % by Weight | Amount |
|---|---|---|
| 1-Isobutyl-1H-imidazo[4,5-c]-quinolin-4-amine | 1.0 | 0.20 g |
| Isostearic acid | 5.0 | 1.00 g |
| Mineral oil | 12.8 | 2.56 g |
| White petrolatum | 65.2 | 13.04 g |
| Cetyl alcohol | 4.0 | 0.80 g |
| Acetylated lanolin | 1.0 | 0.20 g |
| Witconol TM 14 | 3.0 | 0.60 g |
| Aluminum stearate | 8.0 | 1.60 g |

The materials listed above were combined according to following procedure:

The 1-isobutyl-1H-imidazo[4,5-c]quinolin-4-amine and the isostearic acid were placed in a glass jar and heated with stirring until the amine was dissolved. The remaining ingredients were added and the resulting mixture was heated to 65° C. and then mixed while being allowed to cool to room temperature.

EXAMPLE 12

Using the general procedure of Example 11 an ointment containing the following ingredients was prepared.

| | % by Weight | Amount |
|---|---|---|
| 1-Isobutyl-1H-imidazo[4,5-c]-quinolin-4-amine | 1.0 | 0.20 g |
| Isostearic acid | 6.0 | 1.20 g |
| Polyethylene Glycol 400 | 55.8 | 11.16 g |
| Polyethylene Glycol 3350 | 32.6 | 6.52 g |
| Stearyl alcohol | 4.6 | 0.92 g |

EXAMPLES 13-15

Creams of the present invention were prepared using the ingredients shown in Table 3. The Example 1 except that benzyl alcohol was used with the isostearic acid to dissolve the 1-isobutyl-1H-imidazo[4,5-c]quinolin-4-amine.

TABLE 3

| | Example | | |
|---|---|---|---|
| | 13 | 14 | 15 |
| | % by Weight | | |
| Oil Phase | | | |

TABLE 3-continued

| | Example | | |
|---|---|---|---|
| | 13 | 14 | 15 |
| | % by Weight | | |
| 1-Isobutyl-1H-imidazo[4,5-c]-quinolin-4-amine | 5.0 | 5.0 | 4.85 |
| Isostearic acid | 25.0 | 25.0 | 24.3 |
| Benzyl alcohol | 2.0 | 2.0 | 1.94 |
| Cetyl alcohol | 2.2 | 2.2 | 1.16 |
| Stearyl alcohol | 3.1 | 3.1 | 1.75 |
| Petrolatum | 3.0 | — | 2.91 |
| Polysorbate 60 | 3.4 | 3.4 | 4.13 |
| Sorbitan monostearate | 0.6 | 0.6 | 0.73 |
| Stearic acid | — | — | 9.71 |
| Aqueous Phase | | | |
| Glycerin | 2.0 | 2.0 | 1.94 |
| Methylparaben | 0.2 | 0.2 | 0.19 |
| Propylparaben | 0.02 | 0.02 | 0.02 |
| Purified water | 53.48 | 56.48 | 46.39 |

EXAMPLE 16

A cream according to the present invention was prepared from the following ingredients:

| | % by Weight | Amount |
|---|---|---|
| Oil Phase | | |
| 1-Isobutyl-1H-imidazo[4,5-c]-quinolin-4-amine | 4.0 | 0.80 g |
| Isostearic acid | 20.0 | 4.00 g |
| Benzyl alcohol | 2.0 | 0.40 g |
| Cetyl alcohol | 2.2 | 0.49 g |
| Stearyl alcohol | 3.1 | 0.62 g |
| Polysorbate 60 | 3.4 | 0.68 g |
| Sorbitan monostearate | 0.6 | 0.12 g |
| Aqueous Phase | | |
| 1-Isobutyl-1H-imidazo[4,5-c]-quinolin-4-amine | 1.0 | 0.2 g |
| Glycerin | 2.0 | 0.4 g |
| 85% Lactic acid | 1.0 | 0.22 g |
| Methylparaben | 0.2 | 0.04 g |
| Propylparaben | 0.02 | 0.004 g |
| Purified water | 60.48 | 12.0 g |

The materials listed above were combined according to the following procedure:

The isostearic acid and 0.8 g of 1-isobutyl-1H-imidazo[4,5-c]quinolin-4-amine were combined in a glass jar and heated with stirring until the amine had dissolved. The remaining oil phase ingredients were added to this solution and the mixture was heated to about 70° C. The aqueous phase ingredients were weighed into a separate beaker and heated with stirring until the amine and the parabens had dissolved. With both phases at about 70° C., the water phase was added to the oil phase and mixed with a propeller until the mixture cooled to room temperature.

EXAMPLE 17

The formulations of Examples 1–16 of the invention were tested in the hairless mouse skin model described above. The results are summarized in Table 4.

TABLE 4

| Formulation | Number of Determinations | Average % Penetration in 24 Hours |
|---|---|---|
| Example 1 | 8[a] | 21.1 ± 7.2 |
| Example 2 | 16[a] | 14.7 ± 4.2 |
| Example 3 | 4 | 19.5 ± 3.9 |
| Example 4 | 12[a] | 14.3 ± 3.6 |
| Example 5 | 4 | 17.2 ± 2.0 |

TABLE 4-continued

| Formulation | Number of Determinations | Average % Penetration in 24 Hours |
|---|---|---|
| Example 6 | 4 | 36.8 ± 4.3 |
| Example 7 | 4 | 37.5 ± 13.1 |
| Example 8 | 4 | 18.8 ± 2.0 |
| Example 9 | 4 | 22.4 ± 4.8 |
| Example 10 | 8[a] | 32.7 ± 4.1 |
| Example 11 | 4 | 21.6 ± 1.4 |
| Example 12 | 4 | 14.3 ± 0.6 |
| Example 13 | 4 | 58.6 ± 9.2 |
| Example 14 | 8[a] | 39.6 ± 7.4 |
| Example 15 | 4 | 28.9 ± 4.2 |
| Example 16 | 8[a] | 33.0 ± 9.6 |

[a]The determinations were run on different days in groups of 4.

As shown above, the formulations of the invention provide for significant penetration of the active agent.

Several formulations of the present invention were tested in the guinea pig model described above. The results are shown in Table 5.

TABLE 5

| Formulation | Percent Lesion Inhibition | Interferon level (activity/ml) |
|---|---|---|
| Example 1 | 95 | >12,800 |
| Example 2[a] | 43 | 1,333 |
| Example 2 | 40 | 5,066 |
| Example 6 | 29 | 2,133 |
| Example 10 | 30 | 1,866 |
| Example 13 | 60 | 1,200 |
| Example 16 | 50 | 5,800 |

[a]The formulation of Example 2 was tested on two separate occasions.

The formulation of Example 1 was again run in the intravaginal guinea pig model. The protocol was as described above except that the animals were treated twice daily for 4 days starting 6 hours after infection. The results are summarized in Table 6.

TABLE 6

| Formulation | Percent Lesion Inhibition | Interferon Level (activity/ml) |
|---|---|---|
| Example 1 | 71 | 1200 |

EXAMPLE 18

A mixture of 5.9415 g of the 93:7 isooctyl acrylate:acrylamide adhesive copolymer prepared in PREPARATIVE METHOD 2 above, 1.5126 g isostearic acid, 2.0075 g ethyl oleate, 0.3021 g glyceryl monolaurate, 0.2936 g 1-isobutyl-1H-imidazo[4,5-c]quinolin-4-amine (micronized) and 23.7 g of 90:10 ethyl acetate:methanol was placed in a small glass jar. The jar was placed on a horizontal shaker and shaken at room temperature for about 13 hours. The formulation was coated at a thickness of 20 mils onto a 5 mil Daubert 164Z liner. The laminate was oven dried for 3 minutes at 105° F., for 2 minutes at 185° F., and for 2 minutes at 210° F. The resulting adhesive coating contained 59.1 percent 93:7 isooctyl acrylate:acylamide adhesive copolymer, 15.0 percent isostearic acid, 20.0 percent ethyl oleate, 3.0 percent glyceryl monolaurate and 2.9 percent 1-isobutyl-1H-imidazo[4,5-c]quinolin-4-amine. The material was then laminated with 3 mil low density polyethylene backing and die cut into 2.056 cm² patches. Penetration through hairless mouse skin was measured using the diffusion apparatus and method described above. Three independent determinations were carried out. The average penetration in 24 hours was 46.5% of the applied dose.

EXAMPLE 19 and COMPARATIVE EXAMPLE 20

Using the method described in Example 18, the formulations shown below were prepared and the penetration through hairless mouse skin measured. The adhesive used was a copolymer of isooctyl acrylate:acrylic acid (94:6) and had an inherent viscosity of 1.45-1.60 dl/g in ethyl acetate. The solvent used was heptane:isopropanol (70:30). Patches that measured 2.056 cm² were employed. Three independent determinations were carried out and the results were averaged.

| Formulation | Average Percent Penetration in 24 hours |
|---|---|
| Example 19 | |
| 3.0% 1-Isobutyl-1H-imidazo[4,5-c-]-quinolin-4-amine (micronized) 15% Isostearic acid 82% adhesive | 20.5 ± 6.4 |
| Comparative Example 20 | |
| 3.1% 1-Isobutyl-1H-imidazo[4,5-c-]-quinolin-4-amine (micronized) 96.9% adhesive | 4.0 ± 1.5 |

This example shows that a pressure-sensitive adhesive coated sheet material of the invention exhibits superior penetration of 1-isobutyl-1H-imidazo[4,5-c]quinolin-4-amine as compared to one not containing a fatty acid.

EXAMPLES 21–45

Using the method described in Example 18, the formulations shown in Table 7 below were prepared and the penetration through hairless mouse skin was measured. The adhesive used was the copolymer of isooctyl acrylate:acrylamide (93:7), prepared in PREPARATIVE METHOD 1 above. The solvent was 90:10 ethyl acetate:methanol. The 1-isobutyl-1H-imidazo[4,5-c]quinolin-4-amine used was micronized. All formulations were mixed at room temperature unless otherwise indicated. Patches that measured 2.056 cm² were used and four independent determinations were carried out for each formulation unless otherwise indicated and the results were averaged.

TABLE 7

| EXAMPLE | ADHESIVE | AMINE | % By Weight | | | | | HMS |
| | | | ISO | OLEIC | EO | GML | OTHER | |
|---|---|---|---|---|---|---|---|---|
| 21 | 82.1 | 2.9 | 15.0 | | | | | 22.5$^e$ ± 1.76 |
| 22$^a$ | 78.8 | 3.0 | 15.0 | | | 3.2 | | 32.4 ± 1.44 |
| 23$^a$ | 72.0 | 3.0 | 15.0 | | 10.0 | | | 33.8 ± 2.62 |
| 24$^a$ | 75.5 | 3.0 | 15.0 | | 5.0 | 1.5 | | 33.3 ± 2.17 |
| 25$^a$ | 71.9 | 3.0 | | 51.9 | 10.0 | | | 39.9 ± 5.73 |
| 26$^a$ | 76.9 | 3.0 | | 20.1 | | | | 42.2 ± 1.68 |
| 27 | 68.3 | 3.0 | 6.0 | 9.1 | 12.1 | 1.5 | | 33.8 ± 5.38 |
| 28 | 69.7 | 3.0 | 6.0 | 9.1 | 12.1 | | | 26.5 ± 2.61 |
| 29 | 70.0 | 3.0 | 6.0 | 13.0 | 8.0 | | | 44.3 ± 7.69 |
| 30 | 66.9 | 3.0 | | 20.0 | 10.0 | | | 33.2 ± 7.78 |
| 31 | 72.0 | 3.0 | 15.0 | | | | 10.0$^c$ | 28.4 ± 3.48 |
| 32 | 71.9 | 3.0 | | 15.0 | | | 10.1$^d$ | 33.3 ± 2.90 |
| 33 | 65.2 | 3.0 | 6.0 | 13.1 | 8.1 | 1.5 | 3.1$^b$ | 46.3 ± 3.44 |
| 34 | 65.4 | 3.0 | 9.0 | 18.0 | | 1.6 | 3.0$^b$ | 74.5 ± 3.10 |
| 35 | 64.0 | 3.0 | 10.0 | 20.0 | | 1.6 | 1.5$^b$ | 81.4 ± 5.36 |
| 36 | 63.9 | 3.0 | 30.0 | | | 1.5 | 1.6$^b$ | 75.3 ± 5.21 |
| 37 | 63.8 | 3.0 | | 30.1 | | 1.5 | 1.5$^b$ | 80.6 ± 5.41 |
| 38 | 60.1 | 3.1 | 10.0 | 19.8 | 5.5 | 1.5 | | 89.3 ± 4.97 |
| 39 | 58.7 | 3.0 | 10.1 | 19.8 | 5.8 | 1.6 | 1.0$^b$ | 88.0 ± 0.29 |
| 40 | 61.9 | 3.0 | 10.0 | 20.0 | 5.0 | | | 69.0 ± 3.00 |
| 41 | 60.2 | 3.0 | 10.3 | 20.0 | 5.0 | | 1.5$^b$ | 80.0 ± 1.24 |
| 42 | 58.8 | 3.5 | 10.1 | 20.0 | 5.1 | 1.5 | 1.0$^b$ | 86.0 ± 0.78 |
| 43 | 58.3 | 4.0 | 10.2 | 20.2 | 5.0 | 1.5 | 1.0$^b$ | 84.0 ± 2.01 |
| 44 | 57.5 | 4.5 | 9.9 | 20.0 | 5.4 | 1.5 | 1.1$^b$ | 84.0 ± 3.61 |
| 45 | 57.3 | 5.1 | 10.1 | 20.0 | 5.0 | 1.5 | 1.0$^b$ | 87.0 ± 7.23 |

AMINE = 1-Isobutyl-1H-imidazo[4,5-c]quinolin-4-amine
ISO = Isostearic acid
OLEIC = Oleic acid
EO = Ethyl oleate
GML = Glyceryl monolaurate (available from Lauricidin, Inc., Monroe, Michigan, under the trade designation Lauricidin.
HMS = % Penetration in 24 hours in hairless mouse skin model
$^a$Horizontal shaker placed in 40° C. constant temperature room
$^b$N,N-Dimethyldodecylamine-N-oxide
$^c$Isopropyl myristrate
$^d$Diisopropyl adipate
$^e$Used 3 independent determinations

EXAMPLES 46–48

Pressure-Sensitive Adhesive Coated Sheet Materials Prepared Using Unmicronized 1-Isobutyl-1H-imidazo[4,5-c]quinolin-4-amine Using the general method of Example 18 the formulations shown below were prepared. 1-Isobutyl-1H-imidazo[4,5-c]quinolin-4-amine that had been ground with a mortar and pestle was used. The adhesive was the 93:7 isooctyl acrylate:acrylamide copolymer prepared in PREPARATIVE METHOD 1 above. The solvent was 90:10 ethyl acetate:methanol. All formulations were mixed at room temperature.

| | Example | | |
| | 46 | 47 | 48 |
|---|---|---|---|
| 1-Isobutyl-1H-imidazo[4,5-c]-quinolin-4-amine | 5.0 | 3.0 | 3.0 |
| Ethyl oleate | 5.1 | 5.0 | 8.0 |
| Isostearic acid | 10.0 | 10.0 | 6.0 |
| Oleic acid | 20.0 | 20.0 | 13.0 |
| Glyceryl monolaurate | 1.5 | 1.5 | 1.5 |
| N,N-dimethyldodecylamine-N-oxide | 1.0 | 1.1 | 3.0 |

-continued

|  | Example | | |
|---|---|---|---|
|  | 46 | 47 | 48 |
| Adhesive | 57.4 | 59.3 | 65.4 |

The formulations of Examples 46, 47 and 48 were tested in the hairless mouse skin model (4 independent determinations per formulation) and the guinea pig model. Unless otherwise stated, patches that measured 2.056 cm² were employed The cream of Example 1 was run side-by-side with the patches in the guinea pig model. The results are summarized in Table 8.

TABLE 8

| Formulation | % Penetration in 24 hrs | % Lesion Inhibition | Interferon Level (activity/ml) |
|---|---|---|---|
| Example 46 | 36.6 ± 0.88 | 14 | 700 |
|  |  | 86[a] | 4533[a] |
| Example 47 | 39.8 ± 1.44 | 79 | 2266 |
| Example 48 | 30.8 ± 0.88 | 93[a] | >6400[a] |
| Example 1 |  | 93 | >6400 |

[a]Patches measuring 3.88 cm² were employed.

EXAMPLES 49–51

Examples Showing the Effect of Particle Size

Using the general method of Example 18 the formulations shown below, containing 1-isobutyl-1H-imidazo[4,5-c]quinolin-4-amine of different particle size, were prepared and their penetration through hairless mouse skin was measured. The adhesive used was 93:7 isooctyl acrylate:acrylamide copolymer, prepared in PREPARATIVE METHOD 1 above, the solvent used was 90:10 ethyl acetate:methanol, and the formulations were shaken at 40° C. for 72 hours in their preparation. Patches measuring 2.056 cm² were employed and 4 independent determinations were carried out for each formulation.

|  | Example | | |
|---|---|---|---|
|  | 49[a] | 50[b] | 51[c] |
| 1-Isobutyl-1H-imidazo-[4,5-c]quinolin-4-amine | 5.0 | 5.0 | 5.0 |
| Ethyl oleate | 5.0 | 5.2 | 5.1 |
| Isostearic acid | 10.1 | 9.9 | 10.1 |
| Oleic acid | 20.0 | 20.0 | 20.0 |
| Glyceryl monolaurate | 1.5 | 1.5 | 1.5 |
| N,N-Dimethyldodecyl amine N-oxide | 1.0 | 1.0 | 1.0 |
| Adhesive | 57.4 | 57.3 | 57.4 |
| % Penetration in 24 hrs | 40.5 ± 1.99 | 20.1 ± 0.79 | 67.0 ± 1.33 |

[a]Average particle size of 26.8 microns
[b]Average particle size of 32.9 microns
[c]Average particle size of 1.7 microns

EXAMPLE 52

A formulation with the same components in the same proportions as Example 49 was prepared using a different method. The 1-isobutyl-1H-imidazo[4,5-c]-quinolin-4-amine was combined with the oleic and isostearic acids and shaken at 40° C. until there was complete dissolution of the 1-isobutyl-1H-imidazo-[4,5-c]quinolin-4-amine. The remaining ingredients were added and shaken a 40° C. for 72 hours. Patches measuring 2.056 cm² were prepared by the general method of Example 18. Three independent determinations were carried out, and the average penetration in 24 hours was found to be 69.7±1.24 percent of the applied dose.

EXAMPLE 53

A mixture of 2.4734 g 1-isobutyl-1H-imidazo[4,5-c]-quinolin-4-amine 3.3315 g isostearic acid and 6.6763 g oleic acid was prepared. To 1.8738 g of the above mixture was added 2.8750 g of the 93:7 isooctyl acrylate:acryamide adhesive copolymer prepared in PREPARATIVE METHOD 2 above, 0.2548 g of ethyl oleate, 0.0510 g N,N-dimethyl-dodecylamine-N-oxide, 0.0820 g glyceryl monolaurate (from Lauricidin, Inc.) and 14.0457 g of 90:10 ethyl acetate/methanol. The above was shaken for 30 hours at room temperature on a horizontal shaker. Transdermal patches were then prepared generally according to the procedures of Example 18.

What is claimed is:

1. A substantially non-irritating pharmaceutical formulation for topical and/or transdermal administration of the agent 1-isobutyl-1H-imidazo[4,5-c]quinolin-4-amine, which formulation comprises:
   (a) a therapeutically effective amount of 1-isobutyl-1-H-imidazo[4,5-q]quinolin-4-amine; and
   (b) a pharmaceutically acceptable vehicle for said 1-isobutyl-1H-imidazo[4,5-c]quinolin-4-amine, which vehicle comprises isostearic acid in an amount of about 3 percent to about 45 percent by weight based on the total weight of said formulation, said formulation being further characterized in that, when tested according to the hairless mouse skin model the formulation provides a penetration of the agent of at least about 10 percent of the total amount of the agent contained in the formulation in 24 hours.

2. A formulation according to claim 1 wherein said 1-isobutyl-1H-imidazo[4,5-c]quinolin-4-amine is present in an amount of about 0.5 percent to about 9 percent by weight based on the total weight of said formulation.

3. A formulation according to claim 1 in the form of a cream, comprising an oil phase and a water phase in admixture, said oil phase comprising:
   (a) said 1-isobutyl-1H-imidazo[4,5-c]quinolin-4-amine;
   (b) said isostearic acid;
   (c) one or more emollients present in a total amount of about 5 percent to about 30 percent by weight based on the total weight of said formulation; and
   (d) one or more emulsifiers selected from the group consisting of a nonionic surface active agent and a trivalent cationic emulsifier and present in a total amount of about 2 percent to about 14 percent by weight based on the total weight of said formulation;
   said water phase comprising water in an amount of about 45 percent to about 85 percent by weight based on the total weight of said formulation.

4. A formulation according to claim 3 wherein said isostearic acid is present in an amount of about 5 percent to about 25 percent by weight based on the total weight of said formulation.

5. A formulation according to claim 1 in the form of an ointment comprising:
   (a) said 1-isobutyl-1H-imidazo[4,5-c]quinolin-4-amine;
   (b) said isostearic acid in ana mount of about 3 percent to about 25 percent by weight based on the total weight of said formulation; and
   (c) a pharmaceutically acceptable ointment base in an amount of about 60 percent to about 95 percent by weight based on the total weight of said formulation.

6. A formulation according to claim 3 wherein said 1-isobutyl-1H-imidazo[4,5-c]quinolin-4-amine is present in an amount of about 1 percent to about 5 percent by weight based on the total weight of said formulation.

7. A formulation according to claim 4, comprising about 1 percent of said 1-isobutyl-1H-imidazo[4,5-c]quinolin-4-amine, about 10 percent of said isostearic acid, about 2 percent benzyl alcohol, about 2.2 percent cetyl alcohol, about 3.1 percent stearyl alcohol, about 2.55 percent polysorbate 60, about 0.45 percent sorbitan monostearate, about 2 percent glycerin, about 0.2 percent methylparaben, about 0.02 percent propylparaben and about 76.48 percent purified water, all percentages being based on the total weight of said formulation.

8. A formulation according to claim 4, comprising about 1 percent of said 1-isobutyl-1H-imidazo[4,5-c]quinolin-4-amine, about 10 percent of said isostearic acid, about 6 percent cetearyl alcohol, about 2.55 percent polysorbate 60, about 0.45 percent sorbitan monostearate, about 2 percent glycerin, about 0.2 percent methylparaben, about 0.02 percent propylparaben and about 77.78 percent purified water, all percentages being based on the total weight of said formulation.

9. A formulation according to claim 4, comprising about 1 percent of said 1-isobutyl-1H-imidazo[4,5-c]quinolin-4-amine, about 10 percent of said isostearic acid about 2 percent benzyl alcohol, about 1.7 percent cetyl alcohol, about 2.3 percent stearyl alcohol, about 2.55 percent polysorbate 60, about 0.45 percent sorbitan monostearate, about 2 percent glycerin, about 0.2 percent methylparaben, about 0.02 percent propylparaben and about 77.78 percent purified water, all percentages being based on the total weight of said formulation.

10. A formulation according to claim 4, comprising about 5 percent of said 1-isobutyl-1H-imidazo-[4,5-c]quinolin-4-amine, about 25 percent of said isostearic acid, about 2 percent benzyl alcohol, about 2.2 percent cetyl alcohol, about 3.1 percent stearyl alcohol, about 3 percent petrolatum, about 3.4 percent polysorbate 60, about 0.6 percent sorbitan monostearate, about 2 percent glycerin, about 0.2 percent methylparaben, about 0.02 percent propylparaben and about 53.48 percent purified water, all percentages being based on the total weight of said formulation.

11. A formulation according to claim 4, comprising about 1 percent of said 1-isobutyl-1H-imidazo[4,5-c]quinolin-4-amine, about 5 percent of said isostearic acid, about 15 percent petrolatum, about 12.8 percent light mineral oil, about 8 percent aluminum stearate, about 4 percent cetyl alcohol, about 3 percent polyglyceryl-4 oleate, about 1 percent acetylated lanolin, about 0.063 percent propylparaben, about 1 percent Veegum K, about 0.12 percent methylparaben and about 49.02 percent purified water, all percentages being based on the total weight of said formulation.

12. A method of topical and/or transdermal administration of 1-isobutyl-1H-imidazo[4,5-c]quinolin-4-amine for treating a viral disease in a mammal, which method comprises
   (1) placing a formulation according to claim 1 on the skin of a mammal; and
   (2) allowing said formulation to remain in contact with the skin for a sufficient time to permit an effective amount of the 1-isobutyl-1H-imidazo[4,5-c]-quinolin-4-amine to penetrate the skin to achieve the antiviral effect.

13. A method of topical and/or transdermal administration of 1-isobutyl-1H-imidazo[4,5-c]-quinolin-4-amine to induce interferon biosynthesis in a mammal, which method comprises
   (1) placing a formulation according to claim 1 on the skin of a mammal; and
   (2) allowing said formulation to remain in contact with the skin for a sufficient time to permit an effective amount of 1-isobutyl 1H-imidazo[4,5-c]-quinolin-4-amine to penetrate the skin to induce interferon biosynthesis.

* * * * *

UNITED STATES PATENT AND TRADEMARK OFFICE
CERTIFICATE OF CORRECTION

PATENT NO. : 5,238,944
DATED : August 24, 1993
INVENTOR(S) : Helen J. Schultz et al.

It is certified that error appears in the above-indentified patent and that said Letters Patent is hereby corrected as shown below:

On the Title Page, item 75, Inventors should read --Helen J. Schultz, Amit K. Mitra, and Stephen M. Berge--.

Col. 4, line 24, after "cationic" insert --emulsifiers such as aluminum stearate can be included in--.

Col. 7, line 11, "U.S. Pat. No. 24,906" should read --U.S. Patent RE 24,906--.

Col. 11, line 63, after "above" insert --was repeated this time employing 120.0 g isooctyl--.

Col. 12, line 49, after "parabens" insert --were in solution (the temperature reached 80°C). The--.

Col. 16, line 27, "Example 2" should read --Example $2^a$--.

Col. 18, Table 7, Example 30, under the heading "EO", "10.0" should read --10.1--.

Col. 20, line 64, "ana mount" should read --an amount--.

Signed and Sealed this

Ninth Day of May, 1995

Attest:

BRUCE LEHMAN

*Attesting Officer*     *Commissioner of Patents and Trademarks*